(12) United States Patent
Karim et al.

(10) Patent No.: US 10,441,749 B2
(45) Date of Patent: Oct. 15, 2019

(54) CATHETER SECUREMENT DEVICE

(71) Applicant: 3M INNOVATIVE PROPERTIES COMPANY, Saint Paul, MN (US)

(72) Inventors: Naimul Karim, Maplewood, MN (US); Peter M. Eisenberg, Minneapolis, MN (US); Jia Hu, Mounds View, MN (US); Chaodi Li, Woodbury, MN (US); Shilpi K. Sanghi, Saint Paul, MN (US); Jennifer N. Hanson, Saint Paul, MN (US); Thomas G. Skulley, Saint Paul, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 225 days.

(21) Appl. No.: 14/450,318

(22) Filed: Aug. 4, 2014

(65) Prior Publication Data
US 2015/0038912 A1    Feb. 5, 2015

Related U.S. Application Data

(60) Provisional application No. 61/862,284, filed on Aug. 5, 2013.

(51) Int. Cl.
*A61M 25/02*    (2006.01)
*A61M 5/14*    (2006.01)

(52) U.S. Cl.
CPC .......... *A61M 25/02* (2013.01); *A61M 5/1418* (2013.01); *A61M 2025/024* (2013.01);
(Continued)

(58) Field of Classification Search
CPC ............ A61M 25/02; A61M 2025/024; A61M 2025/0246; A61M 2025/0253;
(Continued)

(56) References Cited

U.S. PATENT DOCUMENTS

RE24,906 E    12/1960  Ulrich
3,389,827 A    6/1968  Abere
(Continued)

FOREIGN PATENT DOCUMENTS

GB    2092216    8/1982
GB    2142376    1/1985
(Continued)

OTHER PUBLICATIONS

PCT International Search Report for PCT/US2014/049219 dated Oct. 15, 2014.

*Primary Examiner* — Nathan R Price
*Assistant Examiner* — Anh Bui
(74) *Attorney, Agent, or Firm* — 3M Innovative Properties Company; Trisha D. Adamson

(57) ABSTRACT

A securement device for securing a medical article is disclosed. The securement device comprises a base and a first securing portion comprising a strap that is movable between an open position and a closed position and a connector disposed on the base. The strap cooperates with the connector in the closed position to form an enclosure. The strap further comprises a curvilinear segment that projects inwardly into the enclosure in a convex orientation when the strap is in the closed position. Securement systems for securing medical articles and methods of securing at least a portion of a medical article to a patient are also provided.

18 Claims, 4 Drawing Sheets

(52) U.S. Cl.
CPC .............. *A61M 2025/026* (2013.01); *A61M 2025/0206* (2013.01); *A61M 2025/028* (2013.01); *A61M 2025/0246* (2013.01); *A61M 2025/0253* (2013.01); *A61M 2025/0266* (2013.01); *A61M 2025/0273* (2013.01)

(58) Field of Classification Search
CPC .... A61M 2025/0266; A61M 2025/026; A61M 2025/0273; A61M 2025/028; A61M 2025/0206; A61M 2025/0213; A61M 5/1418

See application file for complete search history.

(56) References Cited

U.S. PATENT DOCUMENTS

| | | |
|---|---|---|
| 3,645,835 A | 2/1972 | Hodgson |
| 4,112,213 A | 9/1978 | Waldman |
| 4,250,880 A | 2/1981 | Gordon |
| 4,310,509 A | 1/1982 | Berglund |
| 4,323,557 A | 4/1982 | Rosso |
| 4,397,647 A | 8/1983 | Gordon |
| 4,595,001 A | 6/1986 | Potter |
| 4,737,410 A | 4/1988 | Kantner |
| 5,088,483 A | 2/1992 | Heinecke |
| 5,160,315 A | 11/1992 | Heinecke |
| 5,593,389 A | 1/1997 | Chang |
| 5,755,225 A | 5/1998 | Hutson |
| 6,209,827 B1 * | 4/2001 | Kawai ............... F16B 21/02 248/49 |
| 6,482,183 B1 | 11/2002 | Pausch |
| 6,565,546 B1 | 5/2003 | Hurst |
| 6,893,655 B2 | 5/2005 | Flanigan |
| 6,994,904 B2 | 2/2006 | Joseph |
| 7,879,013 B2 | 2/2011 | Smith |
| 8,052,648 B2 | 11/2011 | Dikeman |
| 2001/0039399 A1 * | 11/2001 | Bierman ............... A61M 25/02 604/180 |
| 2004/0126413 A1 * | 7/2004 | Sigurjonsson ...... A61F 13/0203 424/445 |
| 2005/0131351 A1 * | 6/2005 | Bierman ............... A61M 25/02 604/174 |
| 2009/0326474 A1 | 12/2009 | Bierman |
| 2011/0112483 A1 | 5/2011 | Smith |
| 2011/0118670 A1 | 5/2011 | Kay |
| 2012/0091181 A1 | 4/2012 | Barnes |
| 2012/0271237 A1 | 10/2012 | Andino |
| 2012/0271240 A1 * | 10/2012 | Andino ............... A61M 25/02 604/180 |
| 2013/0165863 A1 | 6/2013 | Nilson |

FOREIGN PATENT DOCUMENTS

| | | |
|---|---|---|
| WO | WO 98/53872 | 12/1998 |
| WO | WO 99/20334 | 4/1999 |
| WO | WO 2005/104776 | 11/2005 |
| WO | WO 2010-056541 | 5/2010 |
| WO | WO 2010-056543 | 5/2010 |
| WO | WO 2011/060197 | 5/2011 |
| WO | WO 2014-003957 | 1/2014 |

* cited by examiner

CATHETER SECUREMENT DEVICE

BACKGROUND

Various medical treatments often require the use of medical articles and tubing. In many cases the devices or tubing must be secured to a patient's body. For example, it can be necessary to introduce fluids and liquid medications directly into a blood vessel of a patient. For short term general use, a simple intravenous (IV) line can be placed onto a patient's arm. For longer term and more specialized needs, catheters or other devices are used. In another example, a Foley catheter may be necessary for draining urine from a patient's bladder.

Healthcare providers often secure catheters and other devices or tubing to patients during hospital stays or in-home care. Securing the devices aids in proper positioning, which prevents leaks or interruptions in medication dosing, minimizes patient discomfort, and limits tangling, catching, and dislodging of connective tubing due to patient movement.

In order to keep a catheter or other medical articles or tubing properly positioned for the duration of treatment, the medical article may be secured to the patient in a variety of ways. One common way of securing a medical article or tubing is by taping the catheter or medical line to the patient's skin. However, taping can be time consuming and labor intensive. Tape can also collect contaminants and must be frequently removed and replaced. In addition, taping is not necessarily effective in securing a medical article or catheter in place, and removal of the tape may cause undesired motion of the device or catheter. Sutures have also been used to attach a catheter to a patient. With sutures, the catheter is stitched onto the skin. Sutures, however, can be a source of infection, can cause pain and inflammation, and can make it more difficult to clean around the incision site. Sutures also require time and skill to place, and can cause scarring.

Various other securement devices have been developed to obviate some of the fallbacks associated with the use of tape and sutures. Some existing securement devices are generally designed for a specific type or size of catheter or medical article. As a result, multiple securement devices may be needed to accommodate different types or sizes of catheters, e.g., in hospitals and clinical settings. This can add to the cost and complexity of sourcing, inventory, storage, and selection of the securement devices. Additionally, many securement devices still suffer effects of patient movement in which tubing may become kinked or pinched and restrict flow of medication, blood, or urine.

There remains a need for securement devices that accommodate varying sizes of medical articles or tubing and allow patient movement while not disrupting or kinking the tubing.

SUMMARY

The present disclosure is generally directed to medical article securement devices, systems, and methods, and particularly, to universal securement devices, systems, and methods that are adapted to accommodate and reliably secure a large variety of shapes and sizes of catheter systems or other medical articles, particularly elongated medical articles. The securement devices, systems, and methods of the present disclosure are generally robust, easy to use, and are designed to facilitate coupling and decoupling a medical article to and from the system, while also providing means for reliably retaining a medical article, e.g., a catheter system, for a desired treatment period.

One aspect of the present disclosure provides a securement device for securing a medical article. The securement device comprises a base having a longitudinal axis, a top face, and a bottom face. The longitudinal axis defines a longitudinal direction. The securement device further comprises a first securing portion. The first securing portion comprises a strap extending from the top face of the base. The strap is movable between an open position and a closed position. The first securing portion further comprises a connector disposed on the top face of the base. The strap cooperates with the connector in the closed position to form an enclosure. The strap further comprises a curvilinear segment that projects inwardly into the enclosure in a convex orientation when the strap is in the closed position.

In another aspect of the present disclosure, the securement device may further comprise a second securing portion. The second securing portion comprises a frame disposed on the top face of the base and defining an interior aperture. The second securing portion also comprises an entry gap in at least a portion of the frame. In one embodiment, the entry gap in the frame is smaller than the interior aperture defined by the frame. The second securing portion is configured to receive and resiliently retain a generally cylindrical object.

The present application also discloses a securement system for securing a medical article. The securement system comprises a support device and a securement device, as described above. The support device comprises a backing layer comprising a first surface and second surface, opposite the first surface, wherein the backing layer is highly moisture vapor permeable and the first surface of the backing layer is liquid water impermeable. The support device further comprises a cushioning element positioned adjacent the second surface of the backing layer. The support device also comprises a base layer. The base layer comprises a first surface adjacent the cushioning element and a second surface, opposite the first surface of the cushioning element, wherein the backing layer is highly moisture vapor permeable. The base layer is entirely contiguous. The second surface of the base layer comprises an adhesive. The base layer and backing layer connect entirely around the cushioning element. In one embodiment, the bottom face of the base of the securement device is disposed upon the first surface of the backing layer of the support device.

Another aspect of the present disclosure provides a method of securing at least a portion of a medical article to a patient comprising providing the securement system described herein with the strap in the open position. The method further comprises inserting at least a portion of the medical article through the entry gap and into the aperture of the second securing portion. The method further comprises moving the strap from the open position to the closed position such that the enclosure contains at least a portion of the medical article and securing the securement system to the patient.

In one embodiment the medical article is a catheter or catheter tubing. In another embodiment, the medical article is a catheter or catheter tubing connected to a urine bag through urine bag tubing. In another embodiment, the catheter or catheter tubing is secured within the first securing portion and the urine bag tubing is secured within the second securing portion.

Other features and aspects of the present disclosure will become apparent by consideration of the detailed description

Figure 1:
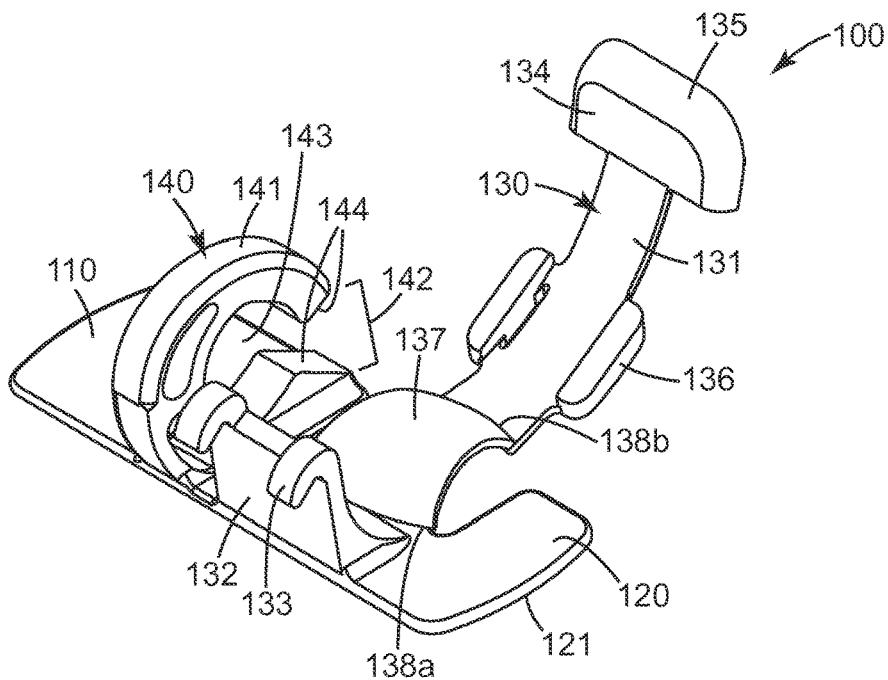
FIG. 1 is a perspective view of a first embodiment of a securement device in an open configuration.

While the above-identified drawings and figures set forth embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of this invention. The figures may not be drawn to scale.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the term "coupled" and variations thereof are used broadly and encompass both direct and indirect couplings. It is to be understood that other embodiments may be utilized, and structural or logical changes may be made without departing from the scope of the present disclosure. Furthermore, terms such as "side," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to medical article securement devices and systems and methods for safely and reliably securing a medical article, such as a catheter system, upon a desired location of a patient's body. The medical article securement systems can be universal to accommodate and reliably secure a large variety of medical articles or class of medical articles (e.g., Foley catheters and PICCs), and can be particularly useful for securing medical articles that need to be secured to a patient over a prolonged period of time, such as weeks or months.

Examples of medical articles that can be employed with the medical article securement devices and systems of the present disclosure include, but are not limited to, connector fittings, catheter systems (e.g., including catheters, catheter hubs, catheter adaptors, etc.), fluid supply lines, other similar articles, or combinations thereof. Examples of catheter systems can include, but are not limited to, Foley catheters, intravenous (IV) catheters, central venous catheters (CVCs), peripherally inserted central catheters (PICCs), arterial catheters, and dialysis catheters.

As used herein, the phrase "generally cylindrical component" is utilized to denote an object, such as a catheter, catheter tubing, or other medical article, having a substantially elliptical outer geometry, as taken along at least a segment of the object's longitudinal axis or centerline. In many cases, the generally cylindrical component will have a substantially circular outer geometry, as taken along the component's entire length; however, this may not always be the case. A non-exhaustive list of generally cylindrical objects includes catheters, tubing such as catheter tubing and urine bag tubing, and connector pieces. Generally cylindrical objects include objects having a conical shape wherein the diameter of the object increases longitudinally along the object. In many cases, the generally annular space will have a substantially circular outer geometry, as taken along the space's entire length; however, this may not always be the case. For example, other geometries may interrupt the substantially circular outer geometry of the space.

The phrase "generally annular" is used to denote a space having a substantially elliptical geometry as taken along at least a segment of the space's longitudinal axis or centerline.

The phrase "entirely contiguous" as used herein means that the surface area is of substantially continuous material construction and is substantially free of large voids, gaps, or perforations in the material construction. On a small scale, a material may still be entirely contiguous even if there are gaps in the material. For example, films, nonwovens, paper, and fabrics could all be formed in a way such that it is entirely contiguous.

The phrase "highly moisture vapor permeable" means that the material transmits moisture vapor at a rate similar to or greater than human skin. For example, using the inverted cup method as described in U.S. Pat. No. 4,595,001, highly moisture vapor permeable means having a rate of at least 300 g/m$^2$/24 hrs at 37° C./100-10% RH.

The phrase "liquid water impermeable" means that if liquid water is put in direct contact with one surface of the material then, under normal atmospheric pressure, it is not readily transported to the opposite surface of the material.

The term "longitudinal" is used to refer to a direction or axis that is generally parallel to the direction in which the securement device and medical article extend and generally parallel to the overall direction of fluid flow, e.g., along a catheter line.

As used herein, "a," "an," "the," "at least one," and "one or more" are used interchangeably.

Figure 2:
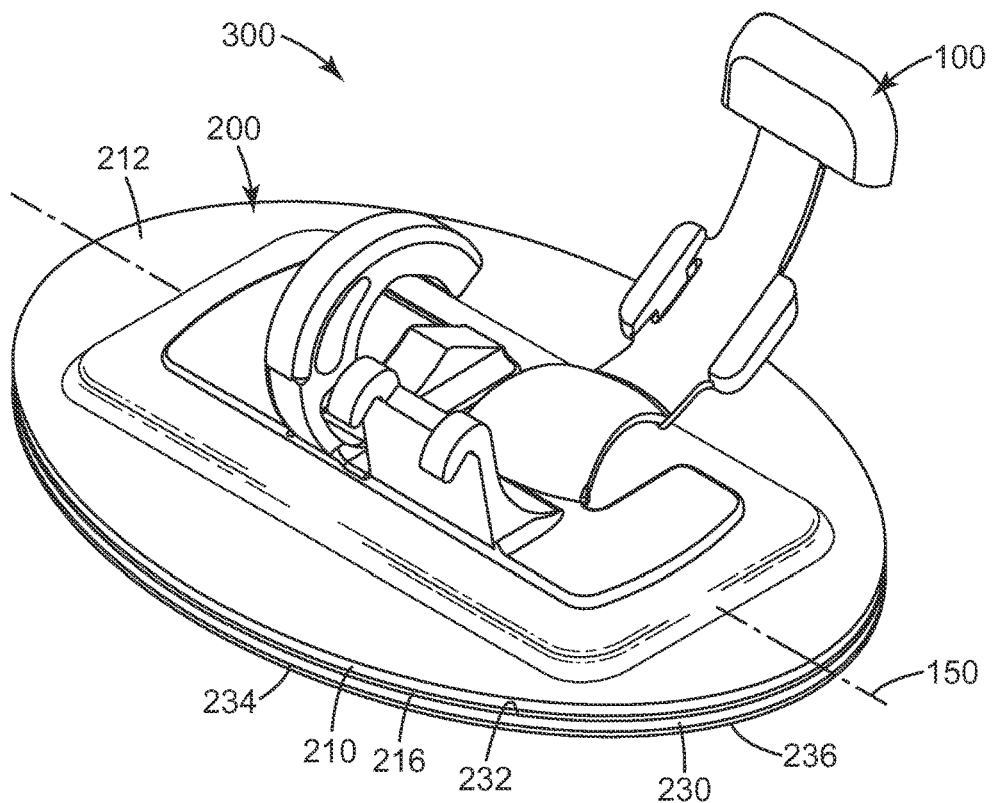
FIG. 2 is a perspective view of a first embodiment of a securement system with the securement device in an open configuration.
Figure 3:
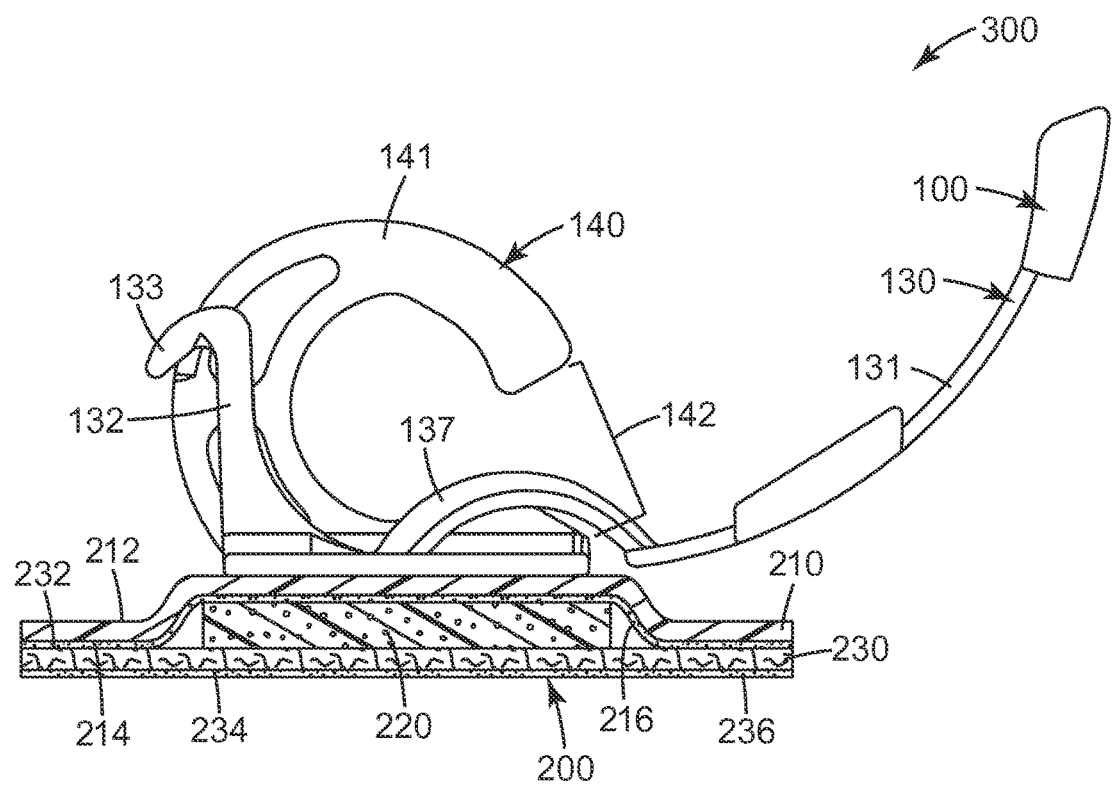
FIG. 3 is a side view of the securement system of FIG. 2.
Figure 4:
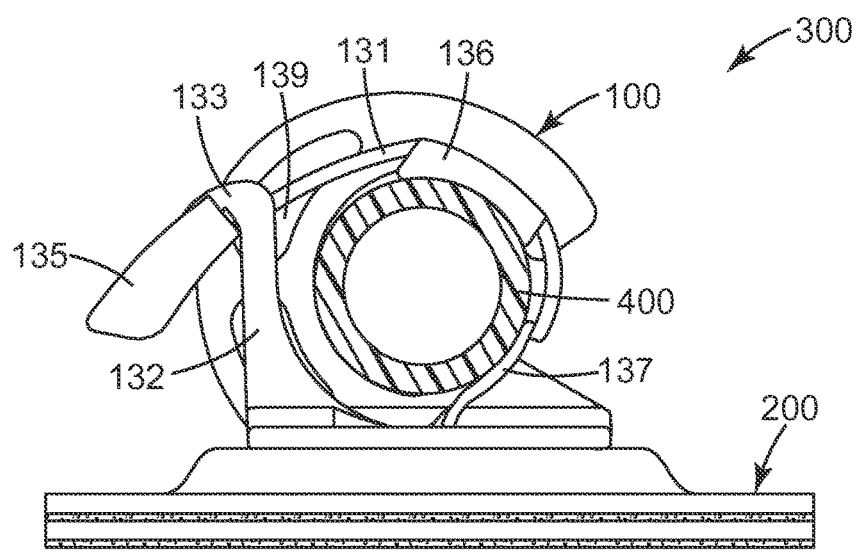
FIG. 4 is a side view of the securement system of FIGS. 2-3 with the securement device in a closed configuration and securing a medical article.

FIG. 1 is a perspective view of a first embodiment of a securement device 100 in an open configuration. FIG. 2 is a perspective view of a first embodiment of a securement system 300 with the securement device 100 in an open configuration. FIG. 3 is a side view of the securement system 300 of FIG. 2. FIG. 4 is a side view of the securement system 300 of FIGS. 2-3 with the securement device 100 in a closed configuration and securing a medical tubing 400.

The securement device 100 comprises a base 110 having a longitudinal axis 150, a top face 120, and a bottom face 121. The longitudinal axis 150 defines a longitudinal direction.

The securement device 100 further comprises a first securing portion 130 comprising a strap 131 extending from the top face 120 of the base 110. The strap 131 is movable between an open position and a closed position. The first securing portion 130 further comprises a connector disposed on the top face 120 of the base 110. In the exemplary embodiment, the connector can comprise one or more posts 132 extending from the top face 120 of the base 110 and one or more catch mechanisms 133. Additional exemplary connectors include latches, hooks, hook and loop constructions, and male-female connectors. The strap 131 cooperates with the connector in the closed position to form an enclosure 139 (shown in FIG. 4). In some embodiments, the enclosure 139 is generally annular in shape. In some embodiments, the strap 131 has a proximal end where the strap 131 is joined to the base 110 and a distal end located away from the base 110 when the strap 131 is in the open position. The strap 131 may optionally further comprise a tab 134 located at the distal end. The tab 134 may optionally comprise a lip 135. In some embodiments, the catch mechanism 133 engages with the tab 134 when the securement device 100 is in a closed position to form the generally annular enclosure 139. In some embodiments, the strap 131 may optionally further comprise one or more wings 136 protruding longitudinally from the strap 131.

In some embodiments, the enclosure 139 of the first securing portion 130 is generally annular in shape. In some embodiments, at least a portion of the enclosure 139 of the first securing portion 130 tapers from a wider shape to a narrower shape in the longitudinal direction. Such tapering may be accomplished by configuring the first securing portion 130 to inherently taper, or the tapering may occur as the strap 131 conforms to the dimensions of the medical article, e.g. medical tubing 400, contained within the enclosure 139 formed when the strap 131 cooperates with the connector in the closed position.

The strap 131 further comprises one or more curvilinear segments 137 that project inwardly into the enclosure 139, e.g. in a convex orientation, when the strap 131 is in the closed position. The curvilinear segment 137 can compress against a tubing or other medical article that is being secured, making it possible to snugly fit tubings or other medical articles of varying dimensions. In some embodiments, when the strap 131 is in the closed position surrounding medical tubing 400, the medical tubing 400 exerts pressure on the curvilinear segments 137 such that the curvilinear segment 137 deforms or partially deforms such that at least a portion of the curvilinear segment 137 become flat or concave with respect to the enclosure 139, as shown in FIG. 4. The curvilinear segment 137 allows the securement device 100 to accommodate medical articles of varying dimensions without pinching or kinking the medical article or tubing because the curvilinear segment 137 can deform as little or as much as needed to accommodate the medical article.

When the securement device 100 is in the open position or is not securing a medical article, the curvilinear segment 137 exhibits a convex curve (with respect to the enclosure 139) in one or more directions. In some embodiments, the curvilinear segment 137 exhibits a convex curve in the direction of the strap 131. In some embodiments, the curvilinear segment 137 exhibits a convex curve both in the direction of the strap 131 and in the longitudinal direction parallel to the longitudinal axis 150 of the base 110. In some embodiments, the curvilinear segment 137 exhibits a convex curve in multiple directions such that it resembles a sphere or a portion of a sphere.

The strap 131 may be permanently coupled to the base 110 and the curvilinear segment 137 via one or more flexible joints 138a, 138b. The curvilinear segment 137 may be positioned anywhere on the strap 131. In some embodiments, the curvilinear segment 137 is positioned between the strap 131 and the base 110 and the curvilinear segment 137 is permanently coupled to both the strap 131 and the base 110. In some embodiments, the curvilinear segment 137 is positioned on the strap 131, e.g. in the middle of the strap 131, such that it is coupled to the strap 131 on either side of the curvilinear segment 137. In some embodiments, the curvilinear segment 137 may be directly and permanently coupled to the base 110 via a flexible joint 138a. Exemplary flexible joints 138a, 138b include hinges and living hinges. In some embodiments the flexible joints 138a, 138b need not be hinges, but may be constructed of a flexible material. In some embodiments, the strap 131 and the curvilinear segment 137 are each independently formed. In some embodiments, the strap 131 and the curvilinear segment 137 are integrally formed from a unitary material. In some embodiments, the flexible joints 138a, 138b, the strap 131, the base 110, and the curvilinear segment 137 may all be constructed integrally from a unitary material.

The securement device 100 further comprises a second securing portion 140, comprising a frame 141 disposed on the top face 120 of the base 110 and defining an interior aperture 143. The second securing portion 140 further comprises an entry gap 142 in at least a portion of the frame 141. The second securing portion 140 may be configured to receive and resiliently retain a generally cylindrical object.

In some embodiments, the entry gap 142 in the frame 141 is smaller than the interior aperture 143 defined by the frame 141 such that a generally cylindrical object can be firmly secured within the interior aperture 143 of the frame 141 via press-fit or snap-fit insertion. The second securing portion 140 is configured such that the maximum width of a generally cylindrical object such as medical tubing 400 (shown in FIG. 4) is greater than the maximum width of the entry gap 142 when the second securing portion 140 is in a non-deflected state (as shown in FIG. 1). As a result, frame edges 144 spread apart or deflect outward to accommodate the generally cylindrical object when it is inserted into entry gap 142 of second securing portion 140. If desired, frame edges 144 may be fabricated to angle inward toward entry gap 142 and interior aperture 143 to facilitate the insertion of a generally cylindrical object and the corresponding deflection of frame edges 144. Thus, in some embodiments, the second securing portion 140 may be a spring clip or may operate similarly to a spring clip.

In some embodiments, frame 141 is fixed such that frame edges 144 do not spread apart or deflect when a generally cylindrical object such as a medical article is pressed into frame 141. In these embodiments, the medical article may deform to allow entry through the entry gap 142 and into the interior aperture 143. In some embodiments, the edges 144 of the frame 141 spread apart or deflect, while at the same time, the medical article deforms, both working cooperatively to allow entry of the medical article through the entry gap 142 and into the interior aperture 143. In some embodiments, the frame 141 further comprises one or more hinges that allow the frame 141 to open and shut for insertion of the medical article into the interior aperture 143. In such embodiments, the frame 141 may or may not comprise the entry gap 142.

In some embodiments, the interior aperture 143 of the frame 141 is generally annular in shape. In some embodiments, frame 141 is generally annular in shape, but it may be any other shape such as square, rectangular, or triangular. The entry gap 142 may be positioned anywhere on the frame 141 of the second securing portion 140. In some embodiments, the entry gap 142 may be positioned directly above the base 110 in the center of the frame 141. In some embodiments, the entry gap 142 may be positioned such that it directly abuts the top face 120 of the base 110. In some embodiments, the entry gap 142 is positioned on the side of the securement device 100 opposite or across the longitudinal axis 150 from the connector, such as in FIG. 1.

In some embodiments, the first securing portion 130 and the second securing portion 140 are each independently coupled to the base 110. Exemplary means of coupling the first securing portion 130 and the second securing portion 140 to the base 110 include but are not limited to, one or more of adhesives, cohesives, magnets, welding (e.g., sonic [e.g., ultrasonic] welding), any thermal bonding or heat sealing technique (e.g., heat and/or pressure applied to one or both of the components to be coupled), other suitable coupling means, or combinations thereof. Additionally, coupling can be accomplished by forming the base 110, the first securing portion 130, and the second securing portion 140 integrally from a unitary material.

In some embodiments, the first securing portion 130 and the second securing portion 140 are spaced a longitudinal distance apart, as shown in FIG. 1. In other embodiments, the first securing portion 130 and the second securing portion 140 may directly abut one another.

The securement device 100 can be applied to a support device 200 to form a securement system 300. The support device 200 can comprise one or more materials that aid in providing a connection of the securement device 100 to the surface to which the securement device 100 is connected. For example, the support device 200 can be a single layer of material with the securement device 100 on one side, and adhesive on the opposite side. Suitable materials could include films, paper, woven, knitted, or nonwoven fabrics. In one embodiment, the support device 200 includes elements that aid in cushioning between the securement device 100 and the surface to which the securement device 100 is connected.

On embodiment of a suitable support device 200 that may be suitable for use with the securement device 100 is described in U.S. Patent Application 61/862,143 filed on the same date and incorporated herein by reference. In one embodiment, the support device 200 comprises a backing layer 210, a base layer 230, and a cushioning element 220 positioned between the backing layer 210 and base layer 230.

The backing layer 210 comprises a first surface 212 and second surface 214, opposite the first surface. The first surface 212 of the backing layer 210 typically faces away from the surface to which the support device 200 attaches. Also, the first surface 212 contacts the bottom face 121 of securement device 100. The backing layer 210 is highly moisture vapor permeable and the first surface 212 of the backing layer 210 is liquid water impermeable.

The cushioning element 220 is placed adjacent the backing layer 210 and base layer 230. The cushioning element 220 provides comfort and helps prevent a securement device 100 from irritating or damaging the underlying surface. Therefore, typically the cushioning element 220 is deformable and compressible. In one embodiment, the cushioning element 220 has a thickness substantially greater than a thickness of the backing layer 210 and base layer 230. In one embodiment, the cushioning element 220 is nonabsorbent. In one embodiment, the cushioning element 220 is highly moisture vapor permeable. In one embodiment, the cushioning element 220 can distribute pressure.

The base layer 230 comprises a first surface 232 adjacent the cushioning element 220 and a second surface 234, opposite the first surface 232 of the cushioning element 220. The second surface 234 of the base layer 230 comprises an adhesive 236. In one embodiment, substantially the entire second surface 234 comprises the adhesive 236. In one embodiment, the adhesive 236 is on a portion of the second surface 234. For example, the adhesive 236 may be pattern coated to the second surface 234 of the base layer 230.

The base layer 230 is entirely contiguous. In one embodiment, the base layer 230 is of continuous and uniform material construction. In one embodiment, the base layer 230 is of substantial uniform thickness across the entire base layer 230. The base layer 230 is highly moisture vapor permeable. In one embodiment, the base layer 230 is liquid water impermeable.

The base layer 230 and backing layer 210 can each comprise one or more layers of materials. In one embodiment, the base layer 230 and backing layer 210 are of substantially the same area. In one embodiment the base layer 230 and backing layer 210 have a larger surface area than the surface area of the cushioning element 220.

To contain the cushioning element 220, the base layer 230 and backing layer 210 connect entirely around the cushioning element 220. In one embodiment, base layer 230, backing layer 210 or both the base layer 230 and backing layer 210 comprise a securing adhesive 216 for connecting the base layer 230 and backing layer 210.

In the exemplified construction, the cushioning element 220 is entirely contained within the structure of the backing layer 210 and base layer 230. The base layer 230 includes an adhesive 236 for securing the support device 200 to a surface, such as skin. The backing layer 210 includes a first surface 212 that is liquid water impermeable, which allows for easy cleaning of the support device 200. Overall, in one embodiment, the backing layer 210, cushioning element 220, and base layer 230 are highly moisture vapor permeable, making the support device 200 well suited for application to skin. Distinguishing from a wound dressing, the support device 200 includes the base layer 230 that is entirely contiguous, which provides significant containment of the cushioning element 220 from liquid.

In one embodiment, the support device 200 can be applied to skin to protect the underlying skin from contact with hard, abrading, or irritating surfaces. In one embodiment, the support device 200 can be applied to skin to protect the skin from applied pressure, which may result in a pressure ulcer on the skin. With the liquid water impermeable backing layer 210, the support device 200 can be easily cleaned. The support device 200 is well suited for application and adhering to skin and can be cleaned without the liquid water penetrating into the cushioning element 220. Limiting absorption of liquid into the cushioning element 220 increases the time that the support device 200 can be worn on the skin without a need for removal and changing.

The securement device 100, can be applied to the first surface 212 of the backing layer 210, adjacent the cushioning element 220. The securement device 100 can be permanently or removably secured to the first surface 212. For example, tape, hook/loop, or adhesives can be used to secure the device 100 to the support device 200. Examples of medical articles include tubing, catheters, ports, or securement devices for securing tubing or catheters. In one embodiment, a securement device 100 such as shown in FIG. 1, is permanently secured to the first surface 212 of the backing layer 210, and the securement device 100 is used to secure tubing or a catheter.

To use the securement device 100 to securing at least a portion of a medical article to a patient, the described strap 131 of securement device 100 is moved to the open position. In one embodiment, at least a portion of a medical article, such as medical tubing 400, is inserted through the entry gap 142 and into the aperture 143 of the second securing portion 140, e.g. via press-fit or snap-fit insertion. The strap 131 is moved from the open position to the closed position such that the enclosure 139 contains at least a portion of the medical article and the securement system 300 is secured to the patient. In one embodiment, the first securing portion 130 is locked in a closed position. In one embodiment, a tab 134 and lip 135 interact with posts 132 and a catch 133 to lock the strap 131 in the closed position. In one embodiment, the curvilinear segment 137 forceably interacts with the medical tubing 400 contained within the enclosure 137 when the strap 131 is in the closed position.

In one embodiment, the securement device 100 is connected to a support device 200 to form a securement system 300. The adhesive 236 on the second surface 234 of the base layer 230 of the support device 200 is applied to the patient to secure the securement system 300. In one embodiment, the securement system 300 is applied to the patient before the medical tubing 400 is inserted into the enclosure 139. In one embodiment, the securement system is applied to the patient after the medical tubing 400 is inserted into the enclosure 139.

In some embodiments, the medical article is a catheter or catheter tubing. In some embodiments, the catheter or catheter tubing is connected to a urine bag through urine bag tubing and the catheter or catheter tubing is secured within the first securing portion 130 and the urine bag tubing is secured within the second securing portion.

Figure 5:
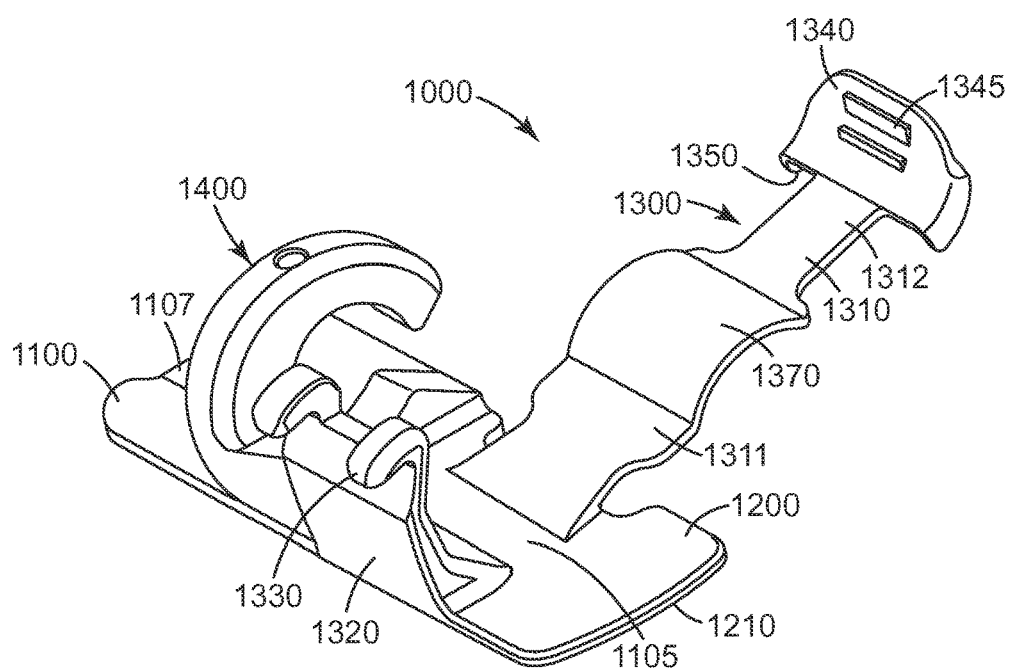
FIG. 5 is a perspective view of a second embodiment of a securement device in an open configuration.
Figure 6:
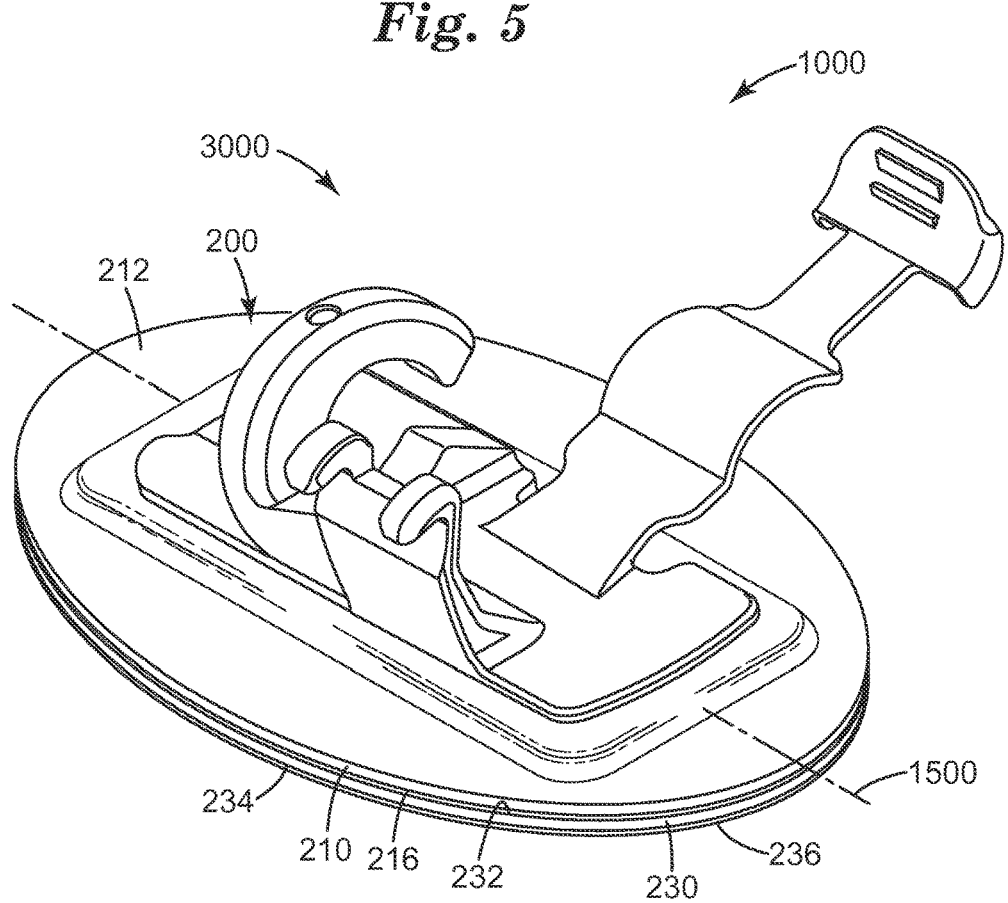
FIG. 6 is a perspective view of a second embodiment of a securement system with the securement device in an open configuration.
Figure 7:
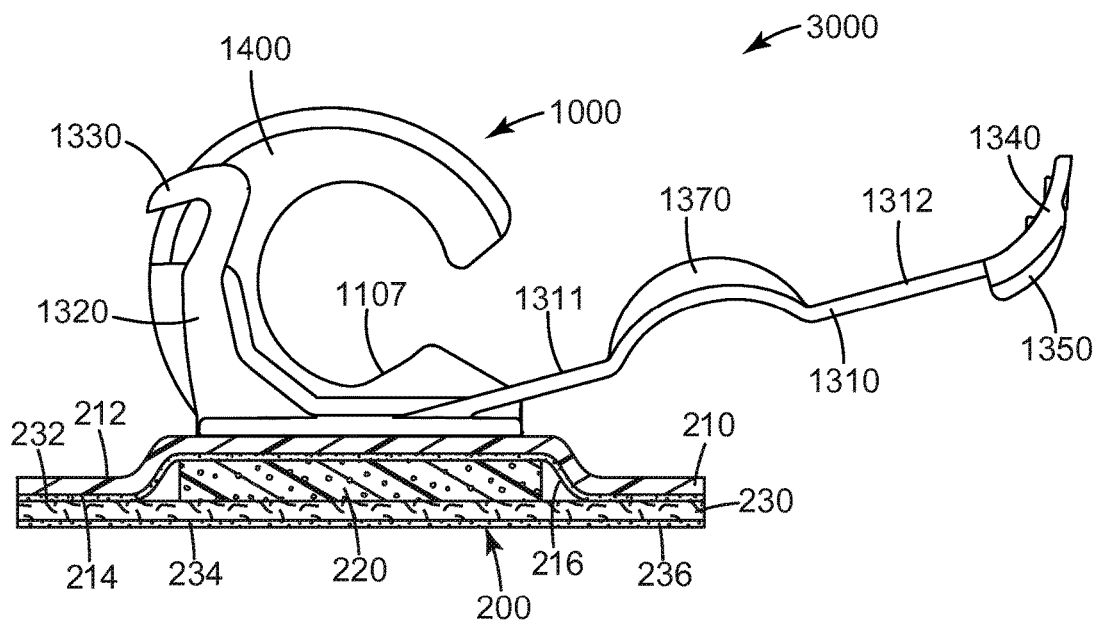
FIG. 7 is a side view of the securement system of FIG. 6.
Figure 8:
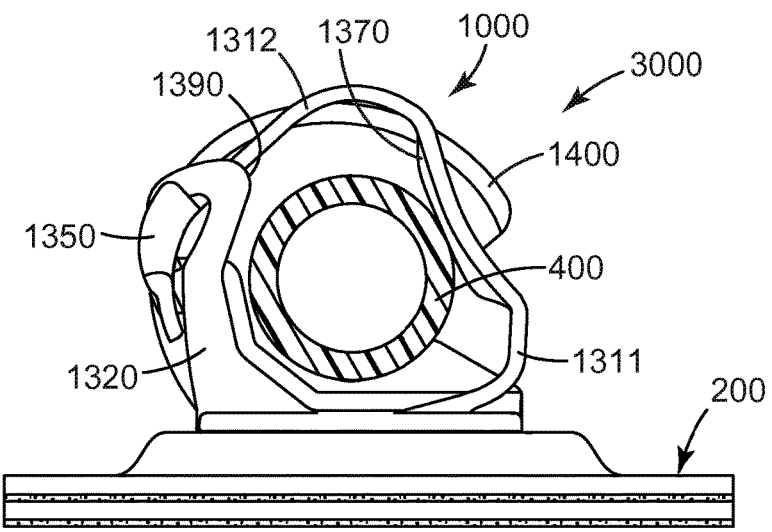
FIG. 8 is a side view of the securement system of FIGS. 6-7 with the securement device in a closed configuration and securing a medical article.

FIG. 5 is a perspective view of a second embodiment of a securement device 1000 in an open configuration. FIG. 6 is a perspective view of a second embodiment of a securement system 3000 with the securement device 1000 in an open configuration. FIG. 7 is a side view of the securement system 3000 of FIG. 6. FIG. 8 is a side view of the securement system 3000 of FIGS. 6-7 with the securement device 1000 in a closed configuration and securing a medical tubing 400. Like features between the first embodiment of the securement system 300 and second securement system 3000 use the same reference numbers. For this second embodiment of the securement system 3000 shown in FIGS. 5-8, the above described features, options, materials apply to the second embodiment of the securement system 3000. Described herein below will be the significant variations of the second embodiment 3000 as compared to the first embodiment 300.

The securement device 1000 comprises a base 1100 having a longitudinal axis 1500, a top face 1200, and a bottom face 1210. The securement device 1000 further comprises a first securing portion 1300 comprising a strap 1310 extending from the top face 1200 of the base 1100. The strap 1310 cooperates with the connector in the closed position to form an enclosure 1390 (shown in FIG. 8). In some embodiments, the strap 1310 has a proximal end where the strap 1310 is joined to the base 1100 and a distal end located away from the base 1100 when the strap 1310 is in the open position.

In the embodiment shown in FIGS. 5-8, the connector can comprises a post 1320 extending from the top face 1200 of the base 1100 and two catch mechanisms 1330. The strap 1310 comprises a tab 1340 located at the distal end and lips 1350 on opposite ends of the tab 1340 to protect against accidental removal of the tab 1340 from the catch 1330. In this embodiment, the tab 1340 includes ridges 1345 to provides a surface for gripping the tab 1340.

The strap 1310 further comprises a curvilinear segment 1370 that project inwardly into the enclosure 1390, e.g. in a convex orientation, when the strap 1310 is in the closed position. The curvilinear segment 1370 can compress against tubing or other medical article 400 (see FIG. 8) that is being secured, making it possible to snugly fit tubing or other medical articles of varying dimensions. In some embodiments, when the strap 1310 is in the closed position surrounding medical tubing 400, the medical tubing 400 exerts pressure on the curvilinear segments 1370 such that the curvilinear segment 1370 deforms or partially deforms such that at least a portion of the curvilinear segment 1370 become flat or concave with respect to the enclosure 1390, as shown in FIG. 8. In the embodiment shown in FIGS. 5-7, the strap 1310 is permanently coupled to the base 1100. The strap 1310 includes a first portion 1311 adjacent the proximal end of the strap 1310 and a second portion 1312 adjacent the distal end of the strap 1310. The curvilinear segment 1370 is positioned between the first portion 1311 of the strap 1310 and the second portion 1312 of the strap 1310.

The securement device 1000 further comprises a second securing portion 1400 substantially similar to the second securing portion 140 described above. In this embodiment, the first securing portion 1300 and the second securing portion 1400 are each independently coupled to the base 110 and are spaced a longitudinal distance apart.

In this embodiment, the top face 1200 of the base 1100 include a first trough 1105 with the enclosure 1390 of the first securing portion 1300 to further support the inserted medical device 400. In this embodiment, the top face 1200 of the base 1100 includes a second trough 1107 adjacent the second securing portion 1400 to support and partially contain the overlying medical device 400.

The securement device 1000 can be applied to a support device 200 substantially similar to the support device 200 described above. The support device 200 can be applied to skin to protect the underlying skin from contact with hard, abrading, or irritating surfaces.

The securement device 1000 can be used and applied substantially similar to the securement device 100 described above.

Securement Device Materials

The securement devices 100, 1000 of the present disclosure can be constructed of any suitable material that allows both appropriate flexibility and rigidity. In some embodiments, the securement devices 100, 1000 of the present disclosure may be constructed of polymeric or elastomeric materials. In some embodiments, the securement devices 100, 1000 of the present disclosure may be constructed of metals, plastics, or composites. Exemplary materials include ABS plastic, polypropylene, polycarbonate, polyethylene, polyvinylchloride, acrylonitrile butadiene styrene, nylon, olefins, acrylics, polyesters, silicones, thermoplastic urethane, thermoplastic elastomers, and the like. In some embodiments, the base 110, 1100 first securing portion 130, 1300 and second securing portion 140, 1400 are all integrally formed from a unitary material. In some embodiments, the base 110, 1100 first securing portion 130, 1300 and second securing portion 140, 1400 may be integrally injection molded from hard plastic to form a unitary piece. In some embodiments, the base 110, 1100 first securing portion 130, 1300 and second securing portion 140, 1400 are independently formed from differing materials. The robustness of the materials used to make the device of the present disclosure can offer facile, reliable, repeatable and secure coupling and decoupling of a medical article to securement device 100, 1000.

The Base

The base 110, 1100 of the present disclosure can be constructed of either rigid or flexible materials. The base 110, 1100 can have any shape or footprint. In some embodiments, the base 110, 1100 has a rectangular shape. In some embodiments, the base 110, 1100 comprises a cut-out portion at the location of the strap 131, 1310.

The Strap

The strap 131, 1310 of the present disclosure can be flexible, particularly, relative to the frame 141 of the present disclosure, and the frame 141, 1410 can be relatively rigid, relative to the strap 131, 1310, even when the frame 141, 1410 and strap 131, 1310 are constructed of the same material. The strap 131, 1310 of the present disclosure can also provide a certain level of flexibility depending on the specific medical article that is being coupled to the securement device 100, because the strap 131, 1310 can be sized and configured to accommodate a variety of medical article configurations and sizes. Additionally, as mentioned above, the curvilinear segment 137, 1370 can allow a single securement device 100, 1000 to accommodate and secure a variety of medical article sizes and shapes. The flexibility of the strap 131, 1310 is generally sufficient to prevent the strap 131, 1310 from breaking (e.g., adjacent its hinge or flexible joint, if employed, as described above), while still being rigid enough to provide structural integrity and to inhibit movement of the medical article when the medical article is coupled to the securement device 100, 1000.

In addition to being formed of the same material as other portions of the securement device 100, 1000 the straps 131, 1310 of the present disclosure can be formed of a variety of materials, including, but not limited to, at least one of a fabric, a woven fibrous web, a nonwoven fibrous web, a knit, a polymeric film, an elastomer, combinations thereof, or a laminate structure comprising any of the above. In some embodiments, the strap 131, 1310 may comprise a hook and loop material or fastener. In some embodiments at least one of the connector and the strap 131, 1310 may comprise hook and loop materials. The straps of the present disclosure generally need to be sufficiently flexible to conform to a portion of the medical article and sufficiently rigid to resist deformation when axial, vertical and/or lateral forces are applied.

In some embodiments, the first securing portion 130, 1300 of the securement device 100, 1000 can comprise two or more straps 131, 1310. In some embodiments, the strap 131, 1310 can comprise two or more pieces joined by a tab 134, 1340 at the distal end of the strap 131, 1310. In some embodiments, the strap 131, 1310 can comprise netting.

As mentioned above, the strap 131, 1310 can comprise a tab 134, 1340 located at the distal end of the strap 131, 1310. Tab 134, 1340 may have a shape, e.g. lip 135, 1350, or a grip that assists a user such as a healthcare worker in moving the strap 131, 1310 from the open position to the closed position. Non-exhaustive exemplary grips include protruding structures disposed on the tab 134, 1340 or embedded in the tab 134, 1340. In some embodiments, the tab 134, 1340 or grip allows movement of the strap 131, 1310 from the open position to the closed position with one hand.

The Curvilinear Segment

The curvilinear segment 137, 1370 can be constructed of any material rigid enough to maintain the shape of the curvilinear segment 137, 1370 when no medical article is present, but flexible enough to allow the curvilinear segment 137, 1370 to deform when a medical article is secured within the enclosure 139, 1390. As described above, the curvilinear segment 137, 1370 can be positioned anywhere on the strap 131, 1310 including between the strap 131, 1310 and the base 110, 1100. As described above, the curvilinear segment 137, 1370 is flexibly joined to one or both of the strap 131, 1310 and base 110, 1100. Additionally, the strap 131, 1310 may include two or more curvilinear segments 137, 1370.

The Frame

The frame 141, 1410 of the second securing portion 140, 1400 is constructed to be relatively rigid, as relates to the strap 131, 1310. However, the frame 141, 1410 must also be flexible enough to allow edges 144 to spread apart or deflect outward to accommodate a generally cylindrical object when it is inserted into entry gap 142 of second securing portion 140, 1400. As described above, in some embodiments, the rigidity of the frame 141, 1410 allows a medical article having a maximum width greater than the width of the entry gap 142, 1420 to be inserted through the entry gap 142, 1420 and firmly secured within the aperture 143 via snap-fit or press-fit insertion. In some embodiments, a user such as a healthcare worker can insert the medical article into the aperture 143 with one hand. In some embodiments, the frame 141, 1410 allows a secure hold on an inserted medical article such that subsequent closure of the strap 131, 1310 around the medical article can be accomplished with one hand.

Support Device Cushioning Element

The cushioning element 220 provides comfort and therefore typically is deformable and compressible. Suitable materials include a foam, sponge, gel, hydrocolloid, nonwoven, woven, or knitted material. In one embodiment the cushioning element 220 is nonabsorbent.

Support Device Backing Layer

The backing layer 210 may include one or more layers of material such as non-woven and woven fibrous webs, knits, films, foams polymeric films and other familiar backing materials. In some embodiments, a transparent substrate is desirable to allow for viewing of the underlying skin or medical device. In one embodiment, the backing layer 210 has high moisture vapor permeability, but generally impermeable to liquid water so that microbes and other contaminants are sealed out from the area under the backing layer 210 and cannot penetrate into the cushioning element 220. One example of a suitable material is a high moisture vapor permeable film such as described in U.S. Pat. Nos. 3,645,835 and 4,595,001, the disclosures of which are herein incorporated by reference. In high moisture vapor permeable film/adhesive composites, the composite should transmit moisture vapor at a rate equal to or greater than human skin such as, for example, at a rate of at least 300 g/m$^2$/24 hrs at 37° C./100-10% RH, or at least 700 g/m$^2$/24 hrs at 37° C./100-10% RH, or at least 2000 g/m$^2$/24 hrs at 37° C./100-10% RH using the inverted cup method as described in U.S. Pat. No. 4,595,001. In one embodiment, the substrate is an elastomeric polyurethane, polyester, or polyether block amide films. These films combine the desirable properties of resiliency, elasticity, high moisture vapor permeability, and transparency. A description of this characteristic of backing layers can be found in issued U.S. Pat. Nos. 5,088,483 and 5,160,315, the disclosures of which are hereby incorporated by reference.

Support Device Base Layer

The base layer 230 provides a surface to which the adhesive 236 is applied to and also provides a surface that contains the cushioning element. In one embodiment, the base layer can be of a construction substantially as described above for the backing layer 210, and therefore includes non-woven and woven fibrous webs, knits, films, foams polymeric films and other familiar backing materials. It may be desirable that the base layer be kept relatively thin to, e.g., improve conformability. For example, the base layer may be formed of polymeric films with a thickness of 200 micrometers or less, or 100 micrometers or less, potentially 50 micrometers or less, or even 25 micrometers or less. The base layer can also be comprised of a combination of two materials, such as, for example, two films (coextruded), film and fabric (woven, knitted, nonwoven). In one embodiment, the base layer 230 has high moisture vapor permeability. In one embodiment, limit introduction of liquid into the cushioning element 220, the base layer 230 is impermeable to liquid water.

Support Device Adhesive

Suitable adhesive for use on the second surface 234 of the base layer 230 for securing the support device 200 to a surface include adhesive that provides acceptable adhesion to skin and is acceptable for use on skin (e.g., the adhesive should preferably be non-irritating and non-sensitizing). Suitable adhesives are pressure sensitive and in certain embodiments have a relatively high moisture vapor transmission rate to allow for moisture evaporation. Suitable pressure sensitive adhesives include those based on acrylates, urethane, hydrogels, hydrocolloids, block copolymers, silicones, rubber based adhesives (including natural rubber, polyisoprene, polyisobutylene, butyl rubber etc.) as well as combinations of these adhesives. The adhesive component may contain tackifiers, plasticizers, rheology modifiers as well as active components including for example an antimicrobial agent.

The pressure sensitive adhesives that may be used may include adhesives that are typically applied to the skin such as the acrylate copolymers described in U.S. Pat. No. RE 24,906, particularly a 97:3 isooctyl acrylate:acrylamide copolymer. Another example may include a 70:15:15 isooctyl acrylate:ethyleneoxide acrylate:acrylic acid terpolymer, as described in U.S. Pat. No. 4,737,410 (Example 31). Other potentially useful adhesives are described in U.S. Pat. Nos. 3,389,827; 4,112,213; 4,310,509; and 4,323,557. Inclusion of medicaments or antimicrobial agents in the adhesive is also contemplated, as described in U.S. Pat. Nos. 4,310,509 and 4,323,557.

Silicone adhesive can also be used. Generally, silicone adhesives can provide suitable adhesion to skin while gently removing from skin. Suitable silicone adhesives are disclosed in PCT Publications WO2010/056541 and WO2010/056543, the disclosure of which are herein incorporate by reference.

The pressure sensitive adhesives may, in some embodiments, transmit moisture vapor at a rate greater to or equal to that of human skin. While such a characteristic can be achieved through the selection of an appropriate adhesive, it is also contemplated that other methods of achieving a high relative rate of moisture vapor transmission may be used, such as pattern coating the adhesive, as described in U.S. Pat. No. 4,595,001. Other potentially suitable pressure sensitive adhesives may include blown-micro-fiber (BMF) adhesives such as, for example, those described in U.S. Pat. No. 6,994,904. The pressure sensitive adhesive used may also include one or more areas in which the adhesive itself includes structures such as, e.g., the microreplicated structures described in U.S. Pat. No. 6,893,655.

Issued U.S. Pat. Nos. 3,645,835 and 4,595,001, the disclosures of which are hereby incorporated by reference, describe methods of making films and methods for testing their permeability. Preferably, the film/adhesive composite should transmit moisture vapor at a rate equal to or greater than human skin. Preferably, the adhesive coated material transmits moisture vapor at a rate of at least 300 g/m2/24 hrs at 37° C./100-10% RH; or in one embodiment at a rate of at least 700 g/m2/24 hrs at 37° C./100-10% RH; or in one embodiment at a rate of at least 2000 g/m2/24 hrs at 37° C./100-10% RH using the inverted cup method as described in U.S. Pat. No. 4,595,001.

Different portions of the support device 200 may include different adhesives, such as disclosed in U.S. Patent Application 61/664,246 filed Jun. 26, 2012 titled "Medical Dressing with Multiple Adhesives." For example, a portion may include an acrylate adhesive while another portion may include a silicone adhesive. In one embodiment, to prevent edge separation, adjacent the perimeter is acrylate adhesive, while near the central portion there is silicone adhesive. In one embodiment, to strongly secure with a device or tubing near the central portion there is acrylate adhesive, while near the perimeter in contact with skin is silicone adhesive.

Optional Components

An optional release liner may be included that covers all or a portion of the adhesives to prevent contamination of the adhesives. In one embodiment, the package that contains the support device 200 may serve as a release liner.

An optional carrier may be included that covers all or a portion of the first surface 212 of the backing layer 210, providing structural support if the backing 210 is thin and highly flexible. The carrier may be removable from the first major surface 212 once the support device 200 is placed on skin. The carrier can be constructed of a variety of materials such as fabric that are woven or knitted, nonwoven material, papers, or film. In one embodiment, the carrier is along the perimeter of the first surface 212 of the backing layer 210 and is removable from the first major surface 212 similar to the carrier used in products such as 3M Tegaderm™ Transparent Film Dressing, available from 3M Company, St. Paul, Minn.

The present disclosure can also provide indicia for use with the securement device 100, 1000 or system 300, 3000 of the present disclosure. In some embodiments the indicia include a representation (e.g., a pictorial representation) of a medical article of interest, such that the indicia mimics the overall shape, appearance and/or configuration of the medical article to provide a visual cue for how to couple the medical article to the securement device or system. In some embodiments, the indicia include directional cues and/or a representation (e.g. a pictorial representation) of a patient's body. Directional cues, such as arrows, may indicate how the system should be oriented relative to another device, structure, or portion of a patient's body. Support devices of the present disclosure can also include such directional cues. Such indicia can enhance the usability of the systems of the present disclosure and can minimize operator errors when applying the systems to patients and coupling medical articles to the devices and systems.

The indicia can include a variety of markings, graphics, or the like, in order to represent a medical article. For example, in some embodiments, the indicia can include a two-dimensional representation of the outline, outer contours, or outer periphery of a medical article. As such, the indicia may be a simplified representation of the medical article, but it will be clear to a user how to orient the medical article relative to the system, based on the caricature or representation of the medical article provided by the indicia. For example, U.S. Patent Application 61/948,142 filed Mar. 5, 2014 describes one example of indicia for use with the securement system 300, 3000.

The following embodiments are intended to be illustrative of the present disclosure and not limiting.

Embodiment 1 is a securement device for securing a medical article, comprising: a base having a longitudinal axis, a top face, and a bottom face, wherein the longitudinal axis defines a longitudinal direction; a first securing portion comprising a strap extending from the top face of the base, wherein the strap is movable between an open position and a closed position; and a connector disposed on the top face of the base; wherein the strap cooperates with the connector in the closed position to form an enclosure; and wherein the strap comprises a curvilinear segment that projects inwardly into the enclosure when the strap is in the closed position.

Embodiment 2 is a securement according to embodiment 1, further comprising a second securing portion comprising a frame disposed on the top face of the base and defining an interior aperture; and an entry gap in at least a portion of the frame.

Embodiment 3 is a securement device according to embodiment 2, wherein the second securing portion is configured to receive and resiliently retain a generally cylindrical object.

Embodiment 4 is a securement device according to any one of embodiments 2 or 3, wherein the entry gap in the frame is smaller than the interior aperture defined by the frame.

Embodiment 5 is a securement device according to any one of embodiments 2-4, wherein the interior aperture of the frame is generally annular in shape.

Embodiment 6 is a securement device according to any one of the preceding embodiments, wherein the enclosure of the first securing portion is generally annular in shape.

Embodiment 7 is a securement device according to any one of the preceding embodiments, wherein at least a portion of the enclosure of the first securing portion tapers from a wider shape to a narrower shape in the longitudinal direction.

Embodiment 8 is a securement device according to any one of embodiments 2-7, wherein the first securing portion and the second securing portion are each independently coupled to the base.

Embodiment 9 is a securement device according to any one of embodiments 2-8, wherein the first securing portion and the second securing portion are spaced a longitudinal distance apart.

Embodiment 10 is a securement device according to any one of the preceding embodiments, wherein the strap has a proximal end where the strap is joined to the base and a distal end located away from the base when the strap is in the open position; and wherein the strap further comprises a tab located at the distal end.

Embodiment 11 is a securement device according to embodiment 8, wherein the tab comprises a lip.

Embodiment 12 is a securement device according to any one of the preceding embodiments, wherein the strap comprises netting.

Embodiment 13 is a securement device according to any one of the preceding embodiments, wherein the strap further comprises one or more wings protruding longitudinally from the strap.

Embodiment 14 is a securement device according to any one of the preceding embodiments, wherein the strap is permanently coupled to the base.

Embodiment 15 is a securement device of according to any one of the preceding embodiments, wherein a flexible joint permanently couples the strap to the base.

Embodiment 16 is a securement device according to any one of the preceding embodiments, wherein the strap is permanently coupled to the curvilinear segment.

Embodiment 17 is a securement device according to any one of the preceding embodiments, wherein a flexible joint permanently couples the strap to the curvilinear segment.

Embodiment 18 is a securement device according to any one of the preceding embodiments, wherein the curvilinear segment is positioned between the strap and the base and the curvilinear segment is permanently coupled to both the strap and the base.

Embodiment 19 is a securement device according to any one of the preceding embodiments, wherein the curvilinear segment is positioned in the middle of the strap such that the strap is on either side of the curvilinear segment.

Embodiment 20 is a securement device according to any one of the preceding embodiments, wherein the strap comprises a first portion at the proximal end and a second portions at the distal end and wherein the curvilinear segment is positioned between the first and second portion of the strap.

Embodiment 21 is a securement device according to any one of the preceding embodiments, wherein a flexible joint permanently couples the curvilinear segment to the base.

Embodiment 22, is a securement device according to any one of the preceding embodiments wherein the flexible joint permanently couples the curvilinear segment to the strap.

Embodiment 23 is a securement device according to any one of embodiments 18, 20, 21, or 22, wherein the flexible joint is a hinge.

Embodiment 24 is a securement device according to embodiment 23, wherein the flexible joint is a living hinge.

Embodiment 25 is a securement device according to any one of the preceding embodiments, wherein the connector comprises a post extending from the top face of the base and a catch mechanism, wherein the catch mechanism engages with the tab when the securement device is in a closed position to form the generally annular enclosure.

Embodiment 26 is a securement device according to any one of embodiments 2-25, wherein the base, the first securing portion, and the second securing portion are formed as a unitary piece.

Embodiment 27 is a securement device according to any one of embodiments 2-26, wherein the strap and the frame are constructed of the same material.

Embodiment 28 is a securement device according to any one of embodiments 2-27, wherein the strap is more flexible than the frame.

Embodiment 29 is a securement device according to any one of the preceding embodiments, wherein the medical article is a catheter or catheter tubing and the enclosure is dimensioned to receive the catheter or catheter tubing.

Embodiment 30 is a securement device according to any one of embodiments 2-29, wherein the medical article is a catheter or catheter tubing connected to a urine bag through urine bag tubing; and wherein the enclosure is dimensioned to receive the catheter or catheter tubing and the aperture is dimensioned to receive the urine bag tubing.

Embodiment 31 is a securement device according to any one of embodiment 2-30, wherein the catheter or catheter tubing is secured within the first securing portion and the urine bag tubing is secured within the second securing portion.

Embodiment 32 is a securement device according to any one of the preceding embodiments, further comprising indicia comprising directional cues, such that the indicia provides a visual cue for orienting the securement device on a patient's body.

Embodiment 33 is a securement system for securing a medical article, comprising: a support device comprising a backing layer comprising a first surface and second surface, opposite the first surface, wherein the backing layer is highly moisture vapor permeable and the first surface of the backing layer is liquid water impermeable; a cushioning element positioned adjacent the second surface of the backing layer; a base layer comprises a first surface adjacent the cushioning element and a second surface, opposite the first surface of the cushioning element, wherein the backing layer is highly moisture vapor permeable; wherein the base layer is entirely contiguous; wherein the second surface of the base layer comprises an adhesive; wherein the base layer and backing layer connect entirely around the cushioning element; and the securement device according to any one of the preceding embodiments.

Embodiment 34 is a securement system according to embodiment 33, wherein the bottom face of the base of the securement device is disposed upon the first surface of the backing layer of the support device.

Embodiment 35 is a securement system according to any one of embodiments 33 or 34, further comprising indicia comprising directional cues, such that the indicia provides a visual cue for orienting the securement system on a patient's body.

Embodiment 36 is a securement system according to embodiment 35, wherein the indicia is disposed on, embedded in, or integrally formed with any portion of the support device or the securement device.

Embodiment 37 is a method of securing at least a portion of a medical article to a patient comprising: providing the securement system according to any one of embodiments 33-36 with the strap in the open position; inserting at least a portion of the medical article through the entry gap and into the aperture of the second securing portion; moving the strap from the open position to the closed position such that the enclosure contains at least a portion of the medical article; and securing the securement system to the patient.

Embodiment 38 is a method according to embodiment 37, wherein the medical article is a catheter or catheter tubing.

Embodiment 39 is a method according to any one of embodiments 37 or 38, wherein the medical article is a catheter or catheter tubing connected to a urine bag through urine bag tubing.

Embodiment 40 is a method according to embodiment 38, wherein the catheter or catheter tubing is secured within the first securing portion and the urine bag tubing is secured within the second securing portion.

Although specific embodiments of this invention have been shown and described herein, it is understood that these embodiments are merely illustrative of the many possible specific arrangements that can be devised in application of the principles of the invention. Numerous and varied other arrangements can be devised in accordance with these principles by those of ordinary skill in the art without departing from the spirit and scope of the invention. Thus, the scope of the present invention should not be limited to the structures described in this application, but only by the structures described by the language of the claims and the equivalents of those structures.

What is claimed is:

1. A securement device for securing a medical article, comprising:
    a base having a longitudinal axis, a top face, and a bottom face, wherein the longitudinal axis defines a longitudinal direction;
    a first securing portion comprising
        a strap extending from the top face of the base, wherein the strap has a length, and wherein the strap is moveable between an open position and a closed position; and
        a connector disposed on the top face of the base;
        wherein the strap cooperates with the connector in the closed position to form an enclosure; and
        wherein the strap comprises a curvilinear segment, wherein the curvilinear segment has a length perpendicular to the longitudinal axis, wherein the length of the curvilinear segment projects inwardly into the enclosure in a convex orientation when the strap is in the closed position, wherein the length of the curvilinear segment is about one-third of the length of the strap, and wherein at least a portion of the curvilinear segment deforms or partially deforms such that at least a portion of the curvilinear segment becomes flat or concave with respect to the enclosure when the strap is in the closed position and when the curvilinear segment is compressed against the medical article.

2. The securement device of claim 1, further comprising a second securing portion comprising
    a frame disposed on the top face of the base and defining an interior aperture; and
    an entry gap in at least a portion of the frame.

3. The securement device of claim 2, wherein the entry gap in the frame is smaller than the interior aperture defined by the frame.

4. The securement device of claim 1, wherein at least a portion of the enclosure of the first securing portion tapers from a wider shape to a narrower shape in the longitudinal direction.

5. The securement device of claim 2, wherein the first securing portion and the second securing portion are each independently coupled to the base and are spaced a longitudinal distance apart.

6. The securement device of claim 1, wherein the strap has a proximal end where the strap is joined to the base and a distal end located away from the base when the strap is in the open position; and wherein the strap further comprises a tab located at the distal end.

7. The securement device of claim 6, wherein the connector comprises a post extending from the top face of the base and a catch mechanism, wherein the catch mechanism engages with the tab when the securement device is in a closed position to form the generally annular enclosure.

8. The securement device of claim 1, wherein a first flexible joint permanently couples the strap to the base and a second flexible joint permanently couples the strap to the curvilinear segment.

9. The securement device of claim 1, wherein the curvilinear segment is positioned between the strap and the base and the curvilinear segment is permanently coupled to both the strap and the base.

10. The securement device of claim 1, wherein the curvilinear segment is positioned in the middle of the strap such that the strap is on either side of the curvilinear segment.

11. The securement device of claim 1, wherein a flexible joint permanently couples the curvilinear segment to the strap.

12. The securement device of claim 2, wherein the base, the first securing portion, and the second securing portion are formed as a unitary piece.

13. The securement device claim 1, further comprising indicia comprising directional cues, such that the indicia provides a visual cue for orienting the securement device on a patient's body.

14. The securement device of claim 1, wherein the bottom face of the base is secured to a support device, wherein the support device comprises:
   a backing layer comprising a first surface and second surface, opposite the first surface, wherein the first surface of the backing layer is liquid water impermeable;
   a cushioning element positioned adjacent the second surface of the backing layer;
   a base layer comprising a first surface adjacent the cushioning element and a second surface, opposite the first surface of the base layer.

15. The securement device of claim 14, wherein the second surface of the base layer comprises an adhesive.

16. The securement device of claim 14, wherein the base layer is entirely contiguous.

17. A securement system for securing a medical article, comprising:
   a support device comprising:
      a backing layer comprising a first surface and second surface, opposite the first surface, wherein the first surface of the backing layer is liquid water impermeable;
      a cushioning element positioned adjacent the second surface of the backing layer;
      a base layer comprising a first surface adjacent the cushioning element and a second surface, opposite the first surface of the base layer;
      wherein the base layer is entirely contiguous;
      wherein the second surface of the base layer comprises an adhesive;
      wherein the base layer and backing layer connect entirely around the cushioning element; and
   a securement device secured to the first surface of the backing layer of the support device, the securement device comprising:
      a base having a longitudinal axis, a top face, and a bottom face, wherein the longitudinal axis defines a longitudinal direction;
      a first securing portion comprising:
         a strap extending from the top face of the base, wherein the strap has a length, and wherein the strap is moveable between an open position and a closed position; and
         a connector disposed on the top face of the base;
      wherein the strap cooperates with the connector in the closed position to form an enclosure; and
      wherein the strap comprises a curvilinear segment, wherein the curvilinear segment has a length perpendicular to the longitudinal axis, wherein the length of the curvilinear segment projects inwardly into the enclosure in a convex orientation when the strap is in the closed position, wherein the length of the curvilinear segment is about one-third of the length of the strap, and wherein at least a portion of the curvilinear segment deforms or partially deforms such that at least a portion of the curvilinear segment becomes flat or concave with respect to the enclosure when the strap is in the closed position and when the curvilinear segment is compressed against the medical article.

18. The securement system of claim 17, further comprising indicia comprising directional cues, such that the indicia provides a visual cue for orienting the securement system on a patient's body.

* * * * *